United States Patent [19]

Ponpipom et al.

[11] 4,228,274

[45] Oct. 14, 1980

[54] 1-SUBSTITUTED GLYCOPYRANOSIDES

[75] Inventors: Mitree M. Ponpipom, North Plainfield; Robert L. Bugianesi, Colonia; Philippe L. Durette, New Providence; Howard M. Katzen, North Plainfield; Tsung-Ying Shen, Westfield, all of N.J.

[73] Assignee: Merck & Co., Inc., Rahway, N.J.

[21] Appl. No.: 922,897

[22] Filed: Jul. 10, 1978

Related U.S. Application Data

[63] Continuation-in-part of Ser. No. 898,265, Apr. 20, 1978, abandoned, which is a continuation of Ser. No. 727,551, Sep. 28, 1976, abandoned.

[51] Int. Cl.$^2$ .......................... C07H 5/06; C07H 5/08
[52] U.S. Cl. .......................................... 536/4; 536/18; 536/22; 536/53
[58] Field of Search .......................... 536/4, 122, 22

[56] References Cited

U.S. PATENT DOCUMENTS

| | | |
|---|---|---|
| 3,243,425 | 3/1966 | Whistler .................................. 536/4 |
| 3,723,617 | 3/1973 | Sutton .................................... 536/4 |
| 3,939,145 | 2/1976 | Gordon .................................... 536/4 |
| 3,939,146 | 2/1976 | Gordon .................................... 536/4 |
| 4,017,608 | 4/1977 | Gordon .................................... 536/4 |

*Primary Examiner*—Johnnie R. Brown
*Attorney, Agent, or Firm*—David L. Rose; Harry E. Westlake

[57] ABSTRACT

The invention disclosed herein relates to novel 1-deoxy-glycopyranosides, preferably 1-deoxy-D-mannopyranosides, having in the 1-position of the pyranoside ring an ω-aminoalkylthio, ω-aminoalkyloxy or ω-aminoalkanoylamino substituent; and to novel processes for preparing these 1-substituted-1-deoxy-glycopyranosides starting with the corresponding tetra-O-acetyl-glycopyranosyl bromide or amine. These ω-amino(alkylthio, alkyloxy or alkanoylamino)-1-deoxy-glycopyranosides, and in particular 1-[(6'-aminohexyl)thio or oxy]-1-deoxy-D-mannopyranosides, possess insulin-like activity.

5 Claims, No Drawings

4,228,274

1-SUBSTITUTED GLYCOPYRANOSIDES

CROSS REFERENCE TO RELATED APPLICATIONS

This application is a continuation-in-part application of co-pending application U.S. Ser. No. 898,265, filed Apr. 20, 1978, abandoned, which in turn is a continuation of co-pending application U.S. Ser. No. 727,551, filed Sept. 28, 1976 abandoned.

BACKGROUND OF THE INVENTION

For many years the appropriate treatment of the hyperglycemia associated with diabetes mellitus has been through the use of injectable insulin. This method has been most satisfactory and has indeed prolonged the lives and sustained the good health of hundreds of thousands of diabetics. The use of injectable insulin has associated with it, however, certain reservations. Since the diabetic condition is a chronic one, it requires constant and, ordinarily, daily injections of insulin. It has been the practice to permit the patient to make his own injections and thus introduce the hazards of improper measurements and non-septic injection techniques. Insulin as now available is subject to deterioration on standing, and unless properly refrigerated, will lose its potency. An additional hazard associated with the use of insulin is that in the achievement of desirably long-acting insulins, suspensions of active insulin (NPH insulin) are frequently utilized, and improper resuspension of these insulins results in more or less than the indicated dosage being administered and measured as a volumetric dose of a varying suspended insulin.

Now these objections can be overcome by using the novel compounds of our invention, i.e., 1-(ω-aminoalkyl)glycopyranosides and 1-deoxy analogs thereof having a 1-(ω-aminoalkylthio) or 1-(ω-aminoalkanoylamino) substituent with a pharmaceutically suitable carrier orally, intravenously, intraperitoneally and intramuscularly. The preferred method is by oral therapy using our invention in the form of tablets containing a stated quantity of the active, stable ingredient.

It is, therefore the principal object of the invention to provide a hypoglycemic composition which obviates the above-mentioned disadvantages that attend the use of insulin, and which upon oral ingestion will rapidly and effectively lower blood sugar levels of the diabetics for sustained periods.

SUMMARY OF THE INVENTION

This invention is concerned generally with novel 1-(ω-aminoalkyl)glycopyranosides and 1-deoxy analogs thereof having a 1-(ω-aminoalkylthio) or 1-ω-aminoalkanoylamino) substituent, which may be represented, in the case of the preferred 1-substituted-D-mannopyranosides, by the following formula:

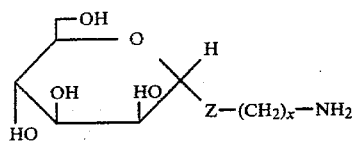

wherein z is oxy, thio or NHCO; and X is an integer from 2 to 8, and with novel processes for their preparation. These novel 1-(ω-aminoalkyl)-glycopyranosides, 1-[(ω-aminoalkyl)thio]-1-deoxy-glycopyranosides, and 1-[(ω-aminoalkanoyl)amino]-1-deoxy-glycopyranosides possess biological activity characteristic of the action of insulin.

This invention is further concerned with hypoglycemic compositions consisting essentially of the foregoing described compounds in admixture with a non-toxic, pharmaceutically-acceptable carrier. A further aspect of the present invention is a method of reducing blood sugar levels in animals comprising administering a therapeutically effective concentration of the inventive compounds in a pharmaceutically suitable carrier intravenously, orally, intraperitoneally and intramuscularly. A further aspect of the present invention is a method of preparing said hypoglycemic pharmacologically active therapeutic compounds.

These 1-substituted glycopyranosides are conveniently prepared utilizing, as starting material, a tetra-O-acetyl-glycopyranosyl bromide in the case of the 1-(ω-aminoalkyl) glycopyranosides, an alkali metal glycopyranosyl mercaptide (i.e. a 1-thio-hexose alkali metal salt) or tetra-O-acetylglycopyranosyl bromide in the case of the 1-[(ω-aminoalkyl)thio]-1-deoxy-glycopyranosides, or a tetraacetyl-glycopyranosylamine in the case of the 1-[(ω-aminoalkanoyl)amino]-1-deoxy-glycopyranosides.

The 1-(ω-aminoalkyl)glycopyranosides are ordinarily prepared by reacting the corresponding tetra-O-acetyl-glycopyranosyl bromide, such as 2,3,4,6-tetra-O-acetyl-α-D-mannopyranosyl bromide; 2,3,4,6-tetra-O-acetyl-α-D-glucopyranosyl bromide; 2,3,4,6-tetra-O-acetyl-α-D-galactopyranosyl bromide; and the like, with an ω-(benzyloxycarbonylamino)-1-alkanol, such as 5-(benzyloxycarbonylamino)-1-pentanol, 6-(benzyloxycarbonylamino)-1-hexanol, 7-(benzyloxycarbonylamino)-1-heptanol, and the like, to form the corresponding 1-(ω-benzyloxycarbonylaminoalkyl)-tetra-O-acetyl-glycopyranoside, such as 1-(5-benzyloxycarbonylaminopentyl)2,3,4,6-tetra-O-acetyl-α-D-mannopyranoside, 1-(6-benzyloxycarbonylaminohexyl)-2,3,4,6-tetra-O-acetyl-α-D-mannopyranoside, 1-(6-benzyloxycarbonylaminohexyl)2,3,4,6-tetra-O-acetyl-β-D-glucopyranoside, 1-(6-benzyloxycarbonylaminohexyl)2,3,4,6-tetra-O-acetyl-β-D-galactopyranoside, 1-(7-benzyloxycarbonylaminoheptyl)2,3,4,6-tetra-O-acetyl-α-D-mannopyranoside, and the like. The reaction is preferably conducted by bringing the reactants together in a substantially anhydrous polar organic solvent such as nitromethane, or mixtures of nitromethane and benzene, and the like, in the presence of mercuric cyanide catalyst, as well as a dehydrating agent such as anhydrous calcium sulfate to insure the maintenance of anhydrous conditions during the reaction, and stirring the resulting mixture at room temperature for a period of approximately 15 hours, at the end of which time the reaction is substantially complete. The reaction mixture is ordinarily evaporated to dryness, extracted with a water-immiscible organic solvent such as chloroform, and the chloroform-soluble material is subjected to chromatography over silica gel to give the 1-(ω-benzyloxycarbonylaminoalkyl)tetra-O-acetyl-glycopyranoside in substantially pure form.

This compound is then reacted, in solution in a lower alkanol such as methanol, with an alkali metal alkoxide such as sodium methoxide, at substantially room temperature for a period of approximately two hours, thereby transesterifying the acetyl groupings to form the corresponding 1-(ω-benzyloxycarbonylaminoalkyl)- glycopyranoside. The slightly alkaline transesterification mixture is neutralized by stirring with an acidic resin, the resin is separated by filtration, and the filtrate is evaporated to give the 1-(ω-benzyloxycarbonylaminoalkyl)glycopyranoside, such as 1-(5-benzyloxycarbonylaminopentyl)α-D-mannopyranoside, 1-(6-benzyloxycarbonylaminohexyl)α-D-mannopyranoside, 1-(6-benzyloxycarbonylaminohexyl)β-D-glucopyranoside, 1-(6-benzyloxycarbonylaminohexyl)β-D-galactopyranoside, 1-(7-benzyloxycarbonylaminoheptyl)α-D-mannopyranoside, and the like.

The 1-(ω-benzyloxycarbonylaminoalkyl)-glycopyranoside is then reacted with hydrogen, thereby removing the benzyloxycarbonyl grouping. The hydrogenation reaction is conveniently conducted by dissolving the 1-(ω-benzyloxycarbonylaminoalkyl)-glycopyranoside in an aqueous alkanol, such as methanol, adding palladium-on-carbon-catalyst, and vigorously agitating the mixture at about 25° C. in contact with hydrogen at atmospheric pressure, under which conditions the hydrogenation reaction is substantially complete in about one hour, to form the corresponding 1-(ω-aminoalkyl)glycopyranoside. The latter is conveniently recovered from the hydrogenation reaction mixture by filtering the mixture through diatomaceous silica, and subjecting the filtered solution to chromatography on a silica gel column to give, in substantially pure form, the 1-(ω-aminoalkyl)-glycopyranoside, such as 1-(5-aminopentyl)α-D-mannopyranoside, 1-(6-aminohexyl)α-D-mannopyranoside, 1-(6-aminohexyl)β-D-glucopyranoside, 1-(6-aminohexyl)-β-D-galactopyranoside, 1-(7-aminoheptyl)α-D-mannopyranoside, and the like.

The 1-[(ω-aminoalkyl)thio]-1-deoxyglycopyranosides are ordinarily prepared by reacting the corresponding tetra-O-acetyl-glycopyranosyl bromide, such as 2,3,4,6-tetra-O-acetyl-α-D-mannopyranosyl bromide, 2,3,4,6-tetra-O-acetyl-α-D-glucopyranosyl bromide, 2,3,4,6-tetra-O-acetyl-α-D-galactopyranosyl bromide, and the like, with thiourea in solution in a substantially anhydrous polar organic solvent such as anhydrous acetone to form the corresponding tetra-O-acetyl-1-deoxy-glycopyranosylisothiouronium bromide. The reaction is preferably conducted by heating the anhydrous mixture of the tetra-O-acetyl-glycopyranosyl bromide, thiourea, and anhydrous acetone at reflux temperature, under which conditions the reaction is ordinarily complete in about two hours. The reaction mixture is cooled, evaporated to dryness in vacuo, and the residual material is crystallized from cold water or acetone to give the said tetra-O-acetyl-1-deoxyglycopyranosylisothiouronium bromide, such as 2,3,4,6-tetra-O-acetyl-1-deoxy-α-D-mannopyranosylisothiouronium bromide, 2,3,4,6-tetra-O-acetyl-1-deoxy-β-glucopyranosylisothiouronium bromide, 2,3,4,6-tetra-O-acetyl-1-deoxy-β-D-galactopyranosylisothiouronium bromide, and the like.

The tetra-O-acetyl-1-deoxy-glycopyranosylisothiouronium bromide is reacted with 1-iodo-ω-trifluoroacetylaminoalkane, such as 1-iodo-5-trifluoroacetylaminopentane, 1-iodo-6-trifluoroacetylaminohexane, 1-iodo-7-trifluoroacetylaminoheptane, and the like. The reaction is conveniently conducted by bringing together an aqueous solution of tetra-O-acetyl-1-deoxy-glycopyranosylisothiouronium bromide containing potassium carbonate and potassium metabisulfite, and an acetone solution containing 1-iodo-ω-trifluoroacetylaminoalkane, and vigorously agitating the resulting mixture at approximately 25° C., under which conditions the reaction is ordinarily complete in about thirty minutes. The acetone is then evaporated, the residual aqueous mixture is extracted with a water-immiscible organic solvent such as chloroform, and the chloroform extract is evaporated to dryness. The residual material is recrystallized from a lower alkanol such as ethanol to give the corresponding 1-[(ω-trifluoroacetylaminoalkyl)thio]-tetra-O-acetyl-1-deoxy-glycopyranoside, such as 1-[(5-trifluoroacetylaminopentyl)thio]-2,3,4,6-tetra-O-acetyl-1-deoxy-α-D-mannopyranoside, 1-[(6-trifluoroacetylaminohexyl)thio]-2,3,4,6-tetra-O-acetyl-1-deoxy-α-D-mannopyranoside, 1-[(6-trifluoroacetylaminohexyl)thio]-2,3,4,6-tetra-O-acetyl-1-deoxy-β-D-glucopyranoside, 1-[(6-trifluoroacetylaminohexyl)thio]-2,3,4,6-tetra-O-acetyl-1-deoxy-β-D-galactopyranoside, 1-[(7-trifluoroacetylaminoheptyl)thio]-2,3,4,6-tetra-O-acetyl-1-deoxy-α-D-mannopyranoside, and the like.

Alternatively, a mixture of 1-thio-hexose salt, e.g. an alkali metal glycopyranosyl mercaptide such as 1-thio-α-D-mannose sodium salt, 1-thio-β-D-mannose sodium salt, 1-thio-β-D-galactose sodium salt, or 1-thio-β-D-glucose sodium salt, an aqueous alkanol, such as aqueous ethanol, and a 1-iodo-ω-trifluoroacetylaminoalkane, such as 1-iodo-5-trifluoroacetylaminopentane, 1-iodo-6-trifluoroacetyl-aminohexane, or 1-iodo-7-trifluoroacetylamino-heptane, is heated, with stirring, at a temperature of about 50° C., under which conditions the reaction is ordinarily complete in about one hour. The reaction mixture is evaporated to dryness, the residual material is acetylated with acetic anhydride and pyridine, and the acetylated mixture is codistilled with toluene, thereby removing pyridine, unreacted acetic anhydride and by-product acetic acid. The residual material is partitioned between dichloromethane and water to give the corresponding 1-[(ω-trifluoroacetylaminoalkyl)thio]-tetra-O-acetyl-1-deoxy-glycopyranoside.

The 1-[(ω-trifluoroacetylaminoalkyl)thio]-tetra-O-acetyl-1-deoxy-glycopyranoside is then reacted in aqueous ethanol solution with a strongly basic anion exchange resin on the hydroxyl cycle, said resin comprising quaternary ammonium groups attached to a styrene-divinylbenzene copolymer. The reaction mixture is stirred vigorously at a temperature of about 25° C., under which conditions hydrolysis of the acetyl and trifluoroacetyl groupings is ordinarily complete in about 15 hours. The insoluble resin is separated from the reaction mixture by filtration, washed with an organic solvent such as methanol, and the solvents evaporated from the combined filtrate and washings to give a syrup which ordinarily crystallizes upon standing to give the corresponding 1-[(ω-aminoallkyl)thio]-1-deoxy-glycopyranoside, such as 1-[(5-aminopentyl)thio]-1-deoxy-α-D-mannopyranoside, 1-[(6-aminohexyl)thio]-1-deoxy-α-D-mannopyranoside, 1-[(6-aminohexyl)thio]-1-deoxy-β-D-mannopyranoside, 1-[(6-aminohexyl)thio]-1-deoxy-β-D-glucopyranoside, 1-[(6-aminohexyl)thio]-1-deoxy-β-D-galactopyranoside, 1-[(7-aminoheptyl)thio]-1-deoxy-β-D-mannopyranoside, and the like.

If desired, tetra-O-acetyl-1-deoxy-glycopyranosylisothiouronium bromide may be reacted with a ω-iodo-1-alkanol, such as 5-iodo-1-pentanol, 6-iodo-1-hexanol, and the like. This reaction, which is carried out in a manner analogous to that employed in the hereinabove description reaction employing 1-iodo-ω-trifluoroacetylaminoalkane in place of the ω-iodo-1-alkanol, results in the formation of the corresponding 1-[(ω-hydroxyalkyl)thio]-tetra-O-acetyl-1-deoxy-glycopyranoside, such as 1-[(5-hydroxypentyl)thio]-2,3,4,6-tetra-O-acetyl-1-deoxy-α-D-mannopyranoside, 1-[(6-hydroxyhexyl)thio]-2,3,4,6-tetra-O-acetyl-1-deoxy-α-D-mannopyranoside, 1-[(6-hydroxyhexyl)thio]-2,3,4,6-tetra-O-acetyl-1-deoxy-β-D-glycopyranoside, 1-[(6-hydroxyhexyl)thio]-2,3,4,6-tetra-O-acetyl-1-deoxy-β-D-galactopyranoside, and the like.

The 1-[ω-hydroxyalkyl)thio]-tetra-O-acetyl-1-deoxy-glycopyranoside is then reacted with p-toluenesulfonylchloride in the presence of a base such as pyridine thereby forming the corresponding p-toluenesulfonate. The reaction is conveniently conducted by dissolving the 1-[(ω-hydroxyalkyl)thio]-tetra-O-acetyl-1-deoxy-glycopyranoside in dry pyridine, adding to this solution a solution of an equivalent amount of p-toluenesulfonyl-chloride in an organic solvent such as chloroform, and stirring the resulting mixture at a temperature of about 0° C., under which conditions the esterification reaction is ordinarily complete in about four hours. The reaction mixture is then poured into ice water, and the aqueous mixture extracted with a water-immiscible organic solvent such as dichloromethane. The combined dichloromethane extracts are washed with an aqueous bicarbonate solution to remove acidic materials, and the organic layer is dried and subjected to vacuum codistillation with toluene to remove pyridine. The residual material is purified by chromatography to give the corresponding 1-[ω-p-toluenesulfonyloxyalkyl)-thio]-tetra-O-acetyl-1-deoxy-glycopyranoside such as 1-[(5-p-toluenesulfonyloxypentyl)thio]-2,3,4,6-tetra-O-acetyl-1-deoxy-α-D-mannopyranoside, 1-[(6-p-toluenesulfonyloxyhexyl)thio]-2,3,4,6-tetra-O-acetyl-1-deoxy-α-D-mannopyranoside, 1-[(6-p-toluene-sulfonyloxyhexyl)thio]-2,3,4,6-tetra-O-acetyl-1-deoxy-β-D-glucopyranoside, 1-[(6-p-toluenesulfonyl-oxyhexyl)thio]-2,3,4,6-tetra-O-acetyl-1-deoxy-β-D-galactopyranoside, and the like.

A mixture of this 1-[ω-p-toluenesulfonyloxyalkyl)thio]-tetra-O-acetyl-1-deoxy-glycopyranoside, an equivalent of sodium cyanide, and an amount of dimethylformamide equal to about ten times the combined weight of these reactants, is heated with stirring at a temperature of about 45° C. while maintaining the mixture under substantially anhydrous conditions; the replacement of the p-toluenesulfonyloxy substituent by the cyano group is ordinarily complete in approximately four hours. The reaction mixture is poured into ice water, the aqueous mixture is extracted with a water-immiscible organic solvent such as dichloromethane, and the dichloromethane extracts are washed with water, dried, and evaporated to dryness. The residual material is acetylated with excess acetic anhydride-pyridine and the acetylated product is purified by chromatography to give the corresponding 1-[(ω-cyanohexyl)-thio]-tetra-O-acetyl-1-deoxy-glycopyranoside, such as 1-[(5-cyanopentyl)thio]-2,3,4,6-tetra-O-acetyl-1-deoxy-α-D-mannopyranoside, 1-[(6-cyanohexyl)thio]-2,3,4,6-tetra-O-acetyl-1-deoxy-α-D-mannopyranoside, 1-[(6-cyanohexyl)thio]-2,3,4,6-tetra-O-acetyl-1-deoxy-β-D-glucopyranoside, 1-[(6-cyanohexyl)thio]-2,3,4,6-tetra-O-acetyl-1-deoxy-β-D-galactopyranoside, and the like.

A solution of this 1-[(ω-cyanohexyl)thio]-tetra-o-acetyl-1-deoxy-glycopyranoside in dry methanol is reacted, at a temperature of 25° C., with a catalytic amount of sodium methoxide, under which conditions the deacetylation reaction is ordinarily complete in about two hours. The reaction solution is neutralized by stirring with an acidic resin, the resin is removed by filtration, and the filtrate is evaporated to give the corresponding 1-[(ω-cyanohexyl)thio-]1-deoxy-glycopyranoside, such as 1-[(5-cyanopentyl)thio]-1-deoxy-α-D-mannopyranoside, 1-[(6-cyanohexyl)thio]-1-deoxy-α-D-mannopyranoside, 1-[(6-cyanohexyl)thio]-1-deoxy-62-D-glucopyranoside, 1-[(6-cyanohexyl)-thio]-1-deoxy-β-D-galactopyranoside, and the like.

A solution of 1-[(ω-cyanoalkyl)thio]-1-deoxy-glycopyranoside in ethanolic ammonia is vigorously agitated in contact with hydrogen at a pressure of about 40 pounds per square inch in the presence of Raney-nickel catalyst and a temperature of about 25° C. Under these conditions, the hydrogenation reaction is ordinarily complete in about eight hours. The hydrogenation mixture is filtered through diatomaceous silica, the filtered solution is evaporated in vacuo, and the residual material subjected to chromatography to give the corresponding 1-[(ω-aminoalkyl)thio]-1-deoxy-glycopyranoside, such as 1-[(6-aminohexyl)thio]-1-deoxy-α-D-mannopyranoside, 1-[(7-aminoheptyl)thio]-1-deoxy-α-D-mannopyranoside, 1-[(7-aminoheptyl)thio]-1-deoxy-β-D-glucopyranoside, 1-[(7-aminoheptyl)-thio]-1-deoxy-β-D-galactopyranoside, and the like.

The 1-[(ω-aminoalkanoyl)amino]-1-deoxy-glycopyranosides are ordinarily prepared by bringing together in solution an organic solvent such as methylene chloride, a hexose pentaacetate, such as D-mannose pentaacetate, D-glucose pentaacetate, D-galactose pentaacetate, and the like, stannic chloride and trimethylsilylazide, and vigorously agitating the resulting mixture at a temperature of about 25° C., under which conditions the reaction is ordinarily complete in about six hours. The methylene chloride reaction solution is washed with water, aqueous sodium bicarbonate solution, and dried, and then evaporated in vacuo to a syrup which ordinarily crystallizes upon standing to give the corresponding tetra-O-acetyl-glycopyranosyl azide, such as 2,3,4,6-tetra-O-acetyl-α-D-mannopyranosyl azide, 2,3,4,6-tetra-O-acetyl-β-D-glucopyranosyl azide, 2,3,4,6tetra-O-acetyl-β-D-galactopyranosyl azide, and the like.

This tetra-O-acetyl-glycopyranosyl azide is dissolved in an organic solvent such as ethyl acetate, Raney-nickel catalyst is added, and the mixture is vigorously agitated with hydrogen at about 25° C., under which conditions the hydrogenation reaction is substantially complete in about six hours. The hydrogenation mixture is filtered through diatomaceous silica, and the filtered solution is evaporated to a syrup which ordinarily crystallizes upon standing in the cold to give the corresponding tetra-O-acetyl-glycopyranosylamine such as 2,3,4,6-tetra-O-acetyl-β-D-mannopyranosylamine, 2,3,4,6-tetra-O-acetyl-β-D-glucopyranosylamine, 2,3,4,6-tetra-O-acetyl-β-D-galactopyranosylamine, and the like.

This tetra-O-acetyl-glycopyranosylamine is reacted with a ω-benzyloxycarbonylaminoalkanoylating agent such as the halide, the anhydride, or the acid in presence of a condensing agent such as dicyclohexylcarbodiimide, as for example 5-benzyloxycarbonylaminopentanoyl chloride, 6-benzyloxycarbonylaminohexanoyl chloride, 7-benzyloxycarbonylaminoheptanoyl chloride, and the like. The reaction is conveniently carried out by bringing the reactants together in solution in an organic solvent such as methylene chloride in the presence of 4-dimethylaminopyridine, and vigorously agitating the mixture at a temperature of about 25° C., under which conditions the reaction is ordinarily complete in about one hour. The methylene chloride reaction mixture, which may be diluted with additional methylene chloride, is washed with aqueous hydrochloric acid solution, with aqueous sodium bicarbonate solution, and with water. The methylene chloride solution is then evaporated to small volume, and the resulting solution is subjected to chromatography over silica gel preferably using a 1:1 mixture of ethylacetate:chloroform as eluant to give the corresponding 1-[ω-benzyloxycarbonylaminoalkanoyl)amino]-tetra-O-acetyl-1-deoxy-glycopyranoside, such as 1-[(5-benzyloxycarbonylaminopentanoyl)amino]-2,3,4,6-tetra-O-acetyl-1-deoxy-β-D-mannopyranoside, 1-[(6-benzyloxycarbonylaminohexanoyl)amino]-2,3,4,6-tetra-O-acetyl-1-deoxy-β-D-mannopyranoside, 1-[(7-benzyloxycarbonylaminoheptanoyl)amino]-2,3,4,6-tetra-O-acetyl-1-deoxy-β-D-mannopyranoside, 1-[(7-benzyloxycarbonylaminoheptanoyl)amino]-2,3,4,6-tetra-O-acetyl-1-deoxy-β-D-glucopyranoside, 1-[(ω-benzyloxycarbonylaminoheptanoyl)amino]-2,3,4,6-tetra-O-acetyl-1-deoxy-β-D-galactopyranoside, and the like.

A solution of 1-[(ω-benzyloxycarbonylaminoalkanoyl)amino]-tetra-O-acetyl-1-deoxy-glycopyranoside in dry methanol is reacted, at a temperature of 25° C. with a catalytic amount of sodium methoxide, under which conditions the deacetylation reaction is ordinarily complete inabout two hours. The reaction solution is neutralized by stirring with an acidic resin, the resin is removed by filtration, and the filtrate is evaporated to give the corresponding 1-[(ω-benzyloxycarbonylaminoalkanoyl)amino]-1-deoxy-glycopyranoside, such as 1-[(5-benzyloxycarbonylaminopentanoyl)amino]-1-deoxy-β-D-mannopyranoside, 1-[(6-benzyloxycarbonylaminohexanoyl)amino]-1-deoxy-β-D-mannopyranoside, 1-[(7-benzyloxycarbonylaminoheptanoyl)amino]-1-deoxy-β-D-mannopyranoside, 1-[(7-benzyloxycarbonylaminoheptanoyl)amino]-1-deoxy-β-D-glucopyranoside, 1-[(7-benzyloxycarbonylaminoheptanoyl)amino]-1-deoxy-β-D-galactopyranoside, and the like.

A mixture of a solution of 1-[(ω-benzyloxycarbonylaminoalkanoyl)amino]-1-deoxy-glycopyranoside in aqueous methanol and a catalytic amount of palladium-on-carbon catalyst is vigorously agitated in contact with a hydrogen atmosphere at atmospheric pressure and at a temperature of about 25° C., under which conditions the hydrogenation reaction is ordinarily complete in about one hour. The hydrogenation mixture is filtered through diatomaceous silica, and the filtered solution is evaporated in vacuo to give the corresponding 1-[(ω-aminoalkanoyl)amino]-1-deoxy-glycopyranoside such as 1-[(5-aminopentanoyl)amino]-1-deoxy-β-D-mannopyranoside, 1-[(6-aminohexanoyl)amino]-1-deoxy-β-D-mannopyranoside, 1-[(7-aminoheptanoyl)-amino]-1-deoxy-β-D-mannopyranoside, 1-[(7-amino-heptanoyl)amino]-1-deoxy-β-D-glucopyranoside, 1-[(7-aminoheptanoyl)amino]-1-deoxy-β-D-galactopyranoside, and the like.

The following examples present illustrative data demonstrating the effectiveness of the novel compounds as insulin-like compounds in vitro.

It is known that fat cells incubated in Krebs-Ringer bicarbonate buffer containing glucose and albumin convert glucose-1-$^{14}$C to $^{14}CO_2$. Addition of insulin causes a stimulation of severalfold of the $^{14}CO_2$ production. This is the basis of the bioassay of insulin-like activity described in J. Gliemann, *Diabetes*, 14, 643(1965). The method for preparing the necessary isolated adipose cells retaining their metabolic activity is described in M. Rodbell, *J. Biol. Chem.*, 239, 375(1964).

The compounds of the present invention have been bioassayed for their insulin-like activity essentially by the process set forth in Gliemann and Rodbell. The results are set forth below in Table 1.

TABLE 1

| In Vitro Fat Cell Bioassay | | |
|---|---|---|
| Compound* | 14-$CO_2$ cpm | Relative Activity % |
| Baseline | 1191 | — |
| Insulin** | 8912 | 100% |
| 1-(6-aminohexyl) α-D-mannopyranoside | 3330 | 28% |
| Baseline | 550 | — |
| Insulin | 2979 | 100% |
| 1-[(6-aminohexyl)thio]-1-deoxy-α-D-mannopyranoside | 2448 | 78% |
| Baseline | 486 | — |
| Insulin | 3164 | 100% |
| 1-[(6-aminohexyl)thio]-1-deoxy-α-D-mannopyranoside | 1288 | 30% |
| Baseline | 542 | — |
| Insulin | 4134 | 100% |
| 1-[(6-aminohexyl)thio]-1-deoxy-α-D-mannopyranoside | 3672 | 87% |
| Baseline | 472 | — |
| Insulin | 5218 | 100% |
| 1-[(6-aminohexyl)thio]-1-deoxy-β-D-mannopyranoside | 4898 | 93% |
| Baseline | 709 | — |
| Insulin | 6413 | 100% |
| 1-[(6-aminohexyl)thio]-1-deoxy-β-D-mannopyranoside | 5177 | 78% |
| Baseline | 486 | — |
| Insulin | 3164 | 100% |
| 1-[(7-aminoheptyl)thio]-1-deoxy-α-D-mannopyranoside | 1088 | 22% |
| Baseline | 542 | — |
| Insulin | 4134 | 100% |
| 1-[(7-aminoheptyl)thio]-1-deoxy-α-D-mannopyranoside | 2533 | 55% |
| Baseline | 757 | — |
| Insulin | 5368 | 100% |
| 1-[(7-aminoheptanoyl)amino]-1-deoxy-β-D-mannopyranoside | 1952 | 26% |

*All compounds were tested at 100 μg./ml.
**Insulin standard at 25 μu/ml.
CALCULATIONS
1. An average CPM value is taken of each group.
2. The average value of Baseline (Buffer control) is subtracted from the average of each of the remaining groups.
3. In order to obtain Relative Activity percentage, the average CPM value for each compound (minus the average CPM value of the control group) is divided by the average CPM value in the insulin standard (minus the average CPM value of the controls), and the resultant value multiplied by 100 to obtain % activity.

The compounds made as described herein possess insulin-like activity and at relatively high doses act like insulin in vivo on the tissues tested, i.e., muscle and adipose. Treatment is by the oral or intravenous route. The preferred route is by oral administration of the compound in a pharmaceutically-acceptable carrier. The actual dosage administered will be determined by such generally recognized factors as the glucose level of the patient's blood, body weight and the severity of the condition being treated which, of course, depends upon the individual patient's physical idiosyncrasies and type of hypoglycemic condition. The compounds are administered in a non-toxic dosage concentration sufficient to lower the blood glucose level to the desired concentration. With these considerations in mind, the daily dosage for a particular patient can be readily determined in accordance with conventional techniques in the medical arts.

When the oral route of administration is used, the new compounds are compounded with a non-toxic excipient, which is edible or potable, and chemically inert to the compounds. The proportion of the excipient should be at least sufficient to separate the particles of the hypoglycemic agent from each other, and to cause quick solution or dispersion of the hypoglycemic composition when contacted with the gastric juice of the stomach. When the excipient is a solid, the amount thereof may be from about 0.3 to about 4 parts for 1 part of the active ingredient.

As solid excipients utilization may be made of lactose, sucrose, starch, pre-gelatinized starch, gum arabic, gum tragacanth and mixtures of these. Suitably, the solid excipient may contain also admixed magnesium stearate, talc, cornstarch, or two or more of these additives to promote separation of the composition from the plunger and mold used in shaping the composition into tablets for use orally.

| HYPOGLYCEMIC TABLET | |
| --- | --- |
| | Weight in Mgs. |
| 1-[(6-aminohexyl)thio]-1-deoxy-β-D-mannopyranoside | 100.0 |
| Sucrose | 25.9 |
| Starch | 22.1 |
| Acacia | 7.8 |
| Talc | 3.1 |
| Magnesium Stearate | 1.5 |
| Stearic Acid | 1.6 |

It will be understood that the glycopyranoside derivative mentioned in the above composition may be substituted by any of the other derivatives described and claimed herein on an equal weight basis. It is also to be considered that the glycopyranosides may be employed alone and in compatible admixtures when preparing various formulations.

In making the tablet the glycopyranoside is mixed with the sucrose and gum acacia, and then with the starch made previously into a paste with a small amount of distilled water. This mixture is dried at low heat and put through a granulator which converts it into a granular powder. This mix is then blended with the talc, magnesium stearate and the stearic acid which act as mold lubricants. The whole is now mixed in a pony mixer or other suitable powder mixing equipment, and then is ready for tableting on any type of tableting machine or for filling into hard gelatin capsules.

When the intravenous route of administration is used the intravenous preparation is simply prepared by dissolving the inventive compounds in distilled water in concentrations dependent upon the particular dosage unit desired.

It will be understood that it is intended to cover all changes and modifications of the examples of the invention herein chosen for the purpose of illustration which do not constitute departures from the spirit and scope of the invention.

The following examples illustrate methods of carrying out the present invention, but it is to be understood that these examples are given for purposes of illustration and not of limitation.

EXAMPLE 1

A mixture of about 35 grams 2,3,4,6-tetra-O-acetyl-α-D-mannopyranosyl bromide, 6.7 grams thiourea and 40 ml. anhydrous acetone is heated at reflux temperature, with stirring and under substantially anhydrous conditions, for a period of approximately two hours. The reaction mixture is cooled and evaporated to dryness in vacuo. The residual material is dissolved in about 50 ml. water, the aqueous solution is washed with 20 ml. ether, and the aqueous layer is separated, cooled to 0° C., and allowed to crystallize at this temperature for about 15 hours. The crystalline material is recovered by filtration, recrystallized from water and dried to give about 25 grams of 2,3,4,6-tetra-O-acetyl-1-deoxy-α-D-mannopyranosylisothiouronium bromide monohydrate; m.p. 125°-128° C.; $[α]_D^{25}+103°$ (c 1, acetone).

To a mixture of about 4.8 grams of 2,3,4,6-tetra-O-acetyl-1-deoxy-α-D-mannopyranosylisothiouronium bromide monohydrate, 1.5 grams potassium carbonate, 2.1 grams potassium metabisulfite, and about 10 ml. water is added, with stirring, a solution of about 2.5 grams of 1-iodo-6-trifluoroacetylaminohexane in 10 ml. acetone. The mixture is stirred at a temperature of about 25° C. for a period of approximately thirty minutes, and the acetone is evaporated from the reaction mixture. The residual aqueous mixture is extracted with chloroform, and the chloroform extract is washed with water, dried over anhydrous sodium sulfate, and evaporated to dryness. The residual material is recrystallized from ethanol to give approximately 4.0 grams of 1-[(6-trifluoroacetylaminohexyl)thio]-2,3,4,6-tetra-O-acetyl-1-deoxy-α-D-mannopyranoside, m.p. 113.5°-115° C., $[α]_D^{25}+77.1$ (c 1, CHCl$_3$).

A mixture of about 2.0 grams 1-[(6-trifluoroacetylaminohexyl)thio]-2,3,4,6-tetra-O-acetyl-1-deoxy-α-D-mannopyranoside, 75 ml. of 50% aqueous ethanol, and 40 milliequivalents of a strongly basic anion exchange resin on the hydroxyl cycle comprising quaternary ammonium groups attached to a styrene-divinylbenzene copolymer, is stirred vigorously at a temperature of about 25° C. for a period of approximately 15 hours. The reaction mixture is filtered, the insoluble resin is washed thoroughly with methanol, and the combined filtrate and washings are evaporated to a syrup, which crystallizes slowly upon standing to give approximately 960 mg. of substantially pure 1-[(6-aminohexyl)thio]-1-deoxy-α-D-mannopyranoside, m.p. 93°-95° C., $[α]_D^{25}+188°$ (c 1, MeOH).

EXAMPLE 2

A mixture of about 600 mg. of 1-thio-β-D-mannose sodium salt, 888 mg. 1-iodo-6-trifluoroacetylaminohexane, and 25 ml. 40% aqueous ethanol, is heated at a temperature of 50° C., with stirring, for a period of approximately one hour. The reaction mixture is cooled and evaporated to dryness in vacuo. The residual material is reacted, at about 25° C., with excess acetic anhydride and pyridine, and the reaction mixture is subjected to distillation in vacuo, followed by vacuum codistillation with toluene thereby substantially completely evaporating the pyridine, unreacted acetic anhydride and by-product acetic acid. The residual material is partitioned between dichloromethane and water. The dichloromethane layer is washed with aqueous sodium thiosulfate, then with cold water, dried, and evaporated to dryness in vacuo. The residual material is recrystallized from ethanol to give about 1.4 grams of 1-[(6-trifluoroacetylaminohexyl)thio]-2,3,4,6-tetra-O-acetyl-1-deoxy-β-D-mannopyranoside; m.p. 121°–122° C.; $[\alpha]_D^{25}$ −47.6° (c 1, chloroform).

A mixture of about 0.9 grams 1-[(6-trifluoroacetylaminohexyl)thio]-2,3,4,6-tetra-O-acetyl-1-deoxy-β-D-mannopyranoside, 46 ml. of 50% aqueous ethanol, 20 milliequivalents of a strongly basic anion exchange resin on the hydroxyl cycle comprising quaternary ammonium groups attached to a styrene-divinylbenzene copolymer, is stirred vigorously at a temperature of about 25° C. for a period of approximately 15 hours. The reaction mixture is filtered, the insoluble resin is washed thoroughly with methanol, and the combined filtrate and washings are evaporated to dryness. The residual solid material is recrystallized from ethanol to give approximately 422 mg. of substantially pure 1-[(6-aminohexyl)thio]-1-deoxy-β-D-mannopyranoside; m.p. 161.8°–163.8° C.; $[\alpha]_D^{25}$ −83.1° (c 1, methanol).

EXAMPLE 3

To a mixture of about 10.5 grams of 2,3,4,6-tetra-O-acetyl-1-deoxy-α-D-mannopyranosylisothiouronium bromide monohydrate, 3.3 grams potassium carbonate, 4.6 grams potassium metabisulfite, and about 20 ml. water, is added, with stirring, a solution of about 20.8 millimoles of 6-iodo-1-hexanol in 20 ml. acetone. The mixture is stirred at a temperature of about 25° C. for a period of approximately 30 minutes, and the acetone is evaporated from the reaction mixture. The residual aqueous mixture is extracted with dichloromethane, and the dichloromethane extract is washed with water, dried over anhydrous sodium sulfate and evaporated to dryness. The residual material is dissolved in chloroform, and the solution is subjected to chromatography on a silica gel column, using a 10:1 mixture of chloroform-ethyl acetate as eluant. The chromatographed product is crystallized from ethanol to give about 6.8 grams of substantially pure 1-[(6-hydroxyhexyl)thio]-2,3,4,6-tetra-O-acetyl-1-deoxy-α-D-mannopyranoside; m.p. 91°–92° C.; $[\alpha]_D^{25}$ +93.6° (c 1, chloroform).

To a solution of about 3.0 grams of 1-[(6-hydroxyhexyl)thio]-2,3,4,6-tetra-O-acetyl-1-deoxy-α-D-mannopyranoside in 6 ml. dry pyridine is added a solution of about 1.4 grams of p-toluenesulfonyl chloride in 3.0 ml. of chloroform. The mixture is stirred at a temperature of about 0° C. for a period of approximately 4 hours. The reaction mixture is poured into ice-water, and the aqueous mixture is extracted with three 30 ml.-portions of dichloromethane. The combined dichloromethane extracts are washed with aqueous sodium bicarbonate solution, with cold water, dried over anhydrous sodium sulfate, and the dried dichloromethane solution is evaporated in vacuo followed by vacuum codistillation with toluene, thereby substantially completely evaporating the pyridine. The residual material is dissolved in dichloromethane, and the solution is subjected to chromatography on a silica gel column, using a 2:1 mixture of ether:petroleum ether as eluant. The chromatographed product is recrystallized from ethanol to give approximately 1.8 grams of 1-[(6-p-toluenesulfonyloxyhexyl)thio]-2,3,4,6-tetra-O-acetyl-1-deoxy-α-D-mannopyranoside; m.p. 73.8°–74.4° C.; $[\alpha]_D^{25}$ +104 (c 1, chloroform).

A mixture of about 0.82 grams of 1-[(6-p-toluenesulfonyloxyhexyl)thio]-2,3,4,6-tetra-O-acetyl-1-deoxy-α-D-mannopyranoside, 0.23 grams sodium cyanide, and 10 ml. dry dimethylformamide, is heated, with stirring, at a temperature of about 45° C. and under substantially anhydrous conditions, for a period of approximately four hours. The reaction mixture is poured into 50 ml. of ice-water, and the aqueous mixture is extracted with three 25 ml. portions of dichloromethane. The combined dichloromethane extracts are washed with ice-water, dried over anhydrous sodium sulfate, and evaporated to dryness in vacuo. The residual material is reacted with excess acetic anhydride and pyridine at a temperature of 25° C. for a period of about 15 hours. The reaction mixture is subjected to distillation in vacuo followed by vacuum codistillation with toluene. The resulting syrup is dissolved in chloroform and the solution subjected to chromatography on silica gel, using 9:1 mixtures of chloroform:ethyl acetate as eluant, to give about 0.5 grams 1-[(6-cyanohexyl)-thio]-2,3,4,6-tetra-O-acetyl-1-deoxy-α-D-mannopyranoside; m.p. 88°–89.2° C.; $[\alpha]_D^{25}$ +91.7 (c 1, chloroform).

A mixture of about 1 gram of 1-[(6-cyanohexyl)thio]-2,3,4,6-tetra-O-acetyl-1-deoxy-α-D-mannopyranoside, 5 ml. dry methanol, and a catalytic amount of sodium methoxide, is stirred at a temperature of about 25° C. for a period of approximately 15 hours. About 0.1 grams of a strongly acidic cation-exchange sulfonated-styrene-divinylbenzene-copolymer resin on the hydrogen cycle is added to the reaction solution; the mixture is stirred, thereby adsorbing the sodium cation on the resin, and the resulting mixture is filtered through diatomaceous silica. The filtered reaction solution is evaporated in vacuo to a syrup which crystallizes from ethyl acetate-ethyl ether. The crystalline material is recovered by filtration and dried to give a substantially quantitative yield of 1-[(6-cyanohexyl)thio]-1-deoxy-α-D-mannopyranoside; m.p. 82°–83° C.; $[\alpha]_D^{25}$ +181° (c 1, methanol).

A mixture of about 200 mg. of 1-[(6-cyanohexyl)thio]-1-deoxy-α-D-mannopyranoside, 200 mg. of Raney nickel catalyst, and 10 ml. of ethanolic ammonia containing 3 grams of ammonia, is vigorously agitated with hydrogen at an initial pressure of approximately 40 pounds/in$^2$ at a temperature of about 25° C. for a period of approximately eight hours. The reaction mixture is filtered through diatomaceous silica, and the filtered solution is evaporated to dryness. The residual material is dissolved in methanol-chloroform (1:1), and the solution is subjected to chromatography on a silica gel column, using a 3:3:1 mixture of chloroform:methanol:ammonium hydroxide as eluant, to give about 120 mg. of 1-[(7-aminoheptyl)thio]-1-deoxy-α-D-mannopyranoside.

EXAMPLE 4

A solution of 10 grams of 2,3,4,6-tetra-O-acetyl-α-D-mannopyranosyl bromide in 50 ml. of dry benzene is added to a solution of 5.01 grams of 6-(benzyoxycarbonylamino)-1-hexanol in 250 ml. of nitromethane containing 5.3 grams mercuric cyanide and 5 grams calcium sulfate. The mixture is stirred at a temperature of about 25° C. for a period of approximately 15 hours, the reaction mixture is filtered, and the filtered solution is evaporated to dryness in vacuo. The residual material is dissolved in chloroform, and the chloroform solution is washed successively with water, with aqueous sodium bicarbonate solution, and again with water, then dried, and the dry chloroform solution is evaporated to a smaller volume. The material, which precipitates, about 2 grams of unreacted 6-(benzyloxycarbonylamino)-1-hexanol, is separated by filtration, and the filtered solution is subjected to chromatography on a silica gel column, using 15% ethyl acetate in chloroform as eluant, to give, as a syrup, about 3.6 grams of 1-(6-benzyloxycarbonylaminohexyl)-2,3,4,6-tetra-O-acetyl-α-D-mannopyranoside.

A solution of about 3 grams of 1-(6-benzyloxycarbonylaminohexyl)-2,3,4,6-tetra-O-acetyl-α-D-mannopyranoside, and 200 mg. of sodium methoxide in 20 ml. of dry methanol is maintained at a temperature of about 25° C. for a period of approximately two hours. The solution is then neutralized by stirring with an acidic resin, filtered, and the filtrate is evaporated in vacuo to give, as a crystalline product, about 2 grams of 1-(6-benzyloxycarbonylaminohexyl)-α-D-mannopyranoside; m.p. 80° C., $[\alpha]_D^{25} +46°$ (c 1, methanol).

A mixture of about 700 mg. of 1-(6-benzyloxycarbonylaminohexyl)-α-D-mannopyranoside, 20 ml. aqueous methanol, and 200 mg. of a 10% palladium-on-carbon catalyst is vigorously agitated with hydrogen at atmospheric pressure and at a temperature of about 25° C. for a period of approximately one hour. The reaction mixture is filtered through diatomaceous silica, and the filtered solution is subjected to chromatography on a silica gel column using a 60:40:10 mixture of chloroform:methanol:50% aqueous ammonium hydroxide as eluant to give about 450 mg. of 1-(6-aminohexyl)-α-D-mannopyranoside, $R_f$ 0.2.

EXAMPLE 5

About 2 ml. stannic chloride is added to a solution of 8 grams of D-mannose pentaacetate and 2.6 ml. trimethylsilyl azide in 180 ml. methylene chloride, and the resulting mixture is stirred at a temperature of about 25° C. for a period of approximately six hours. The reaction solution is diluted with an additional 100 ml. of methylene chloride, and the resulting methylene chloride solution is washed successively with water, with aqueous sodium bicarbonate solution, again with water, and dried over anhydrous sodium sulfate. The dry methylene chloride solution is evaporated in vacuo to a syrup which crystallizes upon standing to give approximately 7.6 grams of 2,3,4,6-tetra-O-acetyl-α-D-mannopyranosyl azide; m.p. 52°–53° C. (after recrystallization from 2-propanol); $[\alpha]_D^{25} +116°$, (c 1.02, chloroform).

To a mixture of about 3.0 grams of 2,3,4,6-tetra-O-acetyl-α-D-mannopyranosyl azide, 0.5 grams Raney nickel catalyst, and 40 ml. ethyl acetate, is vigorously agitated with hydrogen at atmospheric pressure, at a temperature of about 25° C. for a period of about 6.5 hours. The reaction mixture is filtered through diatomaceous silica, and the filtered solution is evaporated in vacuo to a syrup which crystallizes upon standing at a temperature of about 5° C. The crystalline product is recrystallized from 2-propanol to give about 1.7 grams of 2,3,4,6-tetra-O-acetyl-β-D-mannopyranosylamine; m.p. 145°–147° C.; $[\alpha]_D^{25} -9.8°$ (c 1.02, methanol).

A mixture of about 0.87 grams of 2,3,4,6-tetra-O-acetyl-β-D-mannopyranosylamine, 0.75 grams 7-benzyloxycarbonylaminoheptanoyl chloride, 62 mg. 4-dimethylaminopyridine, and 20 ml. methylene chloride, is stirred at a temperature of about 25° C. for a period of approximately one hour. The reaction mixture is diluted with an additional 20 ml. methylene chloride, and the resulting mixture washed successively with 1 N aqueous hydrochloric acid solution, with aqueous sodium bicarbonate solution, and then with water. The methylene chloride solution is evaporated to small volume, and then subjected to chromatography over silica gel using a 1:1 mixture of ethyl acetate:chloroform as eluant to give about 0.9 grams of 1-[(7-benzyloxycarbonylaminoheptanoyl)-amino]-2,3,4,6-tetra-O-acetyl-1-deoxy-β-D-mannopyranoside, $[\alpha]_D -7.6 \pm 0.6$ (c 1.58, chloroform).

A solution of about 50 mg. of sodium methoxide 1.13 grams of 1-[(7-benzyloxycarbonylaminoheptanoyl)amino]-2,3,4,6-tetra-O-acetyl-1-deoxy-β-D-mannopyranoside, and 25 ml. dry methanol, is maintained at a temperature of about 25° C. for a period of approximately two hours. The reaction solution is neutralized by stirring with an acidic resin, filtered, and the filtrate evaporated in vacuo to give a crystalline material which, upon recrystallization from methanol, gives about 0.76 grams of 1-[(7-benzyloxycarbonylaminoheptanoyl)amino]-1-deoxy-β-D-mannopyranoside; m.p. 169°–172° C., $[\alpha]_D -7.4 \pm 0.3$ (c 1.0, methanol).

A mixture of about 200 mg. of 1-[(7-benzyl-oxycarbonylaminoheptanoyl)amino]-1-deoxy-β-D-mannopyranoside, 10 ml. of aqueous methanol, and 80 mg. of 10% palladium-on-carbon catalyst is vigorously agitated with hydrogen at atmospheric pressure and at a temperature of about 25° C. for a period of approximately one hour. The reaction mixture is filtered through diatomaceous silica, and the filtered solution is evaporated in vacuo to a crystalline material, which is triturated with ethanol, recovered by filtration and dried to give approximately 125 mg. of 1-[(7-aminoheptanoyl)amino]-1-deoxy-β-D-mannopyranoside; m.p. 162° C. (dec.), $[\alpha]_D -19.4° \pm 0.5°$ (c 1.59, water).

Various changes and modifications may be made in carrying out the present invention without departing from the spirit and scope thereof. Insofar as these changes and modifications are within the purview of the annexed claims, they are to be considered as part of this invention.

What is claimed is:

1. A hypoglycemic compound selected from the group consisting of 1-[(ω-aminoalkyl)thio]-1-deoxyglycopyranosides and 1-[(ω-aminoalkanoyl)amino]-1-deoxy-glycopyranosides, wherein said alkyl contains 2 to 8 carbon atoms and said alkanoyl contains 3 to 9 carbon atoms.

2. The compound, as defined in claim 1, having the chemical name 1-[(6-aminohexyl)thio]-1-deoxy-α-D-mannopyranoside.

3. The compound, as defined in claim 1, having the chemical name 1-[(6-aminohexyl)thio]-1-deoxy-β-D-mannopyranoside.

4. The compound, as defined in claim 1, having the chemical name 1-[(7-aminoheptyl)thio]-1-deoxy-α-D-mannopyranoside.

5. The compound, as defined in claim 1, having the chemical name 1-[(7-aminoheptanoyl)amino]-1-deoxy-β-D-mannopyranoside.

* * * * *